United States Patent
Otsubo

(10) Patent No.: US 7,156,831 B2
(45) Date of Patent: Jan. 2, 2007

(54) DISPOSABLE PULL-ON UNDERGARMENT

(75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/967,484

(22) Filed: Oct. 18, 2004

(65) Prior Publication Data

US 2005/0055006 A1   Mar. 10, 2005

Related U.S. Application Data

(63) Continuation of application No. 09/415,525, filed on Oct. 8, 1999, now abandoned.

(30) Foreign Application Priority Data

Oct. 14, 1998   (JP)   ................. 10-292202

(51) Int. Cl.
*A61F 13/15*   (2006.01)
*A61F 13/20*   (2006.01)

(52) U.S. Cl. ................. 604/385.27; 604/385.24; 604/385.25; 604/385.29

(58) Field of Classification Search ........... 604/385.01, 604/385.24–385.3
See application file for complete search history.

(56) References Cited

U.S. PATENT DOCUMENTS

| | | | |
|---|---|---|---|
| 4,802,884 A | 2/1989 | Froidh et al. | |
| 4,892,528 A * | 1/1990 | Suzuki et al. | .......... 604/385.27 |
| 4,897,084 A | 1/1990 | Ternstron et al. | |
| 5,092,861 A | 3/1992 | Nomura et al. | |
| 5,447,508 A | 9/1995 | Numano et al. | |
| 5,576,091 A | 11/1996 | Zajaczkowski et al. | |
| 5,649,919 A | 7/1997 | Roessler et al. | |
| 5,743,994 A | 4/1998 | Roessler et al. | |
| 5,830,203 A | 11/1998 | Suzuki et al. | |
| 6,013,065 A | 1/2000 | Suziki et al. | |
| 6,050,984 A | 4/2000 | Fujioka et al. | |
| 6,179,820 B1 | 1/2001 | Fernfors | |

FOREIGN PATENT DOCUMENTS

| | | |
|---|---|---|
| EP | 0 412 579 A1 | 2/1991 |
| EP | 0 623 331 A2 | 11/1994 |
| EP | 0 787 474 A1 | 8/1997 |
| WO | 96/34588 * | 11/1996 |

* cited by examiner

*Primary Examiner*—Michele Kidwell
(74) *Attorney, Agent, or Firm*—Butzel Long

(57) ABSTRACT

A disposable pull-on undergarment includes a pair of leg-openings provided with elastic members. Each of the elastic members extends along a peripheral edge of the leg-openings and is spaced outward from each of transversely opposite side edges of the core by a distance which is larger in any one of the front and rear waist regions than the other of them as measured in a substantially middle zone of a crotch region. Along a folding line Y extending in the transverse direction to divide the undergarment in upper and lower halves, the undergarment is folded toward any one of the front and rear waist regions in which the distance is relatively large.

2 Claims, 3 Drawing Sheets

DISPOSABLE PULL-ON UNDERGARMENT

RELATED APPLICATIONS

The present application is a continuation application of U.S. patent application Ser. No. 09/415,525, filed Oct. 8, 1999 now abandoned which claims priority under 35 U.S.C. §119 to Japanese Patent Application No. 10-292202, filed Jun. Oct. 14, 1998.

BACKGROUND OF THE INVENTION

This invention relates to a disposable pull-on undergarment such as a disposable diaper for absorption and containment of bodily wastes.

A disposable pull-on undergarment is well known, in which a liquid-absorbent core is disposed between a topsheet and a backsheet, a waist-opening is provided with an elastic member extending under tension along a peripheral edge thereof, a crotch region extending between front and rear waist regions is formed at its transversely opposite sides with leg-openings, respectively, and the respective leg-openings are provided along peripheral edges thereof with elastic members under tension.

Japanese Patent Application Disclosure Gazette (Kokai) No. Hei3-82467 discloses a disposable pull-on undergarment, in which respective leg-openings are provided with elastic means each comprising first and second elastic members. Respective intermediate portions of the first and second elastic members extend across a liquid-absorbent core in a crotch region. Lateral extensions of the first elastic member which are continuous with opposite ends of its intermediate portion extend substantially over front halves of the respective leg-openings' peripheral edges while lateral extensions of the second elastic member which are continuous with opposite ends of its intermediate portion extend substantially over rear halves of the respective leg-openings' peripheral edges. The first elastic member presents a stretch stress higher than a stretch stress presented by the second elastic member. In the known undergarment, the lateral extensions of the first elastic member extending substantially over the front halves of the leg-openings' peripheral edges can be put against the wearer's skin more tightly than the lateral extensions of the second elastic member. The intermediate portions of the first and second elastic members serve to lift the crotch region of the undergarment toward the wearer's skin.

The undergarment provided around the leg-openings with elastic members, a distance by which the elastic member extending in the rear waist region should be spaced from the opposite side edge of the absorbent core has usually been dimensioned to be larger than a distance by which the elastic member extending in the front waist region should be spaced from the side edges of the absorbent core. When the elastic member is relieved of the tension and the undergarment is left free, a contractile force of the elastic member extending in the front waist region forcibly contracts the absorbent core in the longitudinal direction. As a result, the absorbent core is apt to be creased.

The undergarment disclosed in the Japanese Patent Application Disclosure Gazette (Kokai) No. Hei3-82467 is arranged so that the first elastic member presents a relatively high stretch stress and therefore the portion of the absorbent core lying in the front waist region is significantly creased. Such portion of the absorbent core formed with creases has an apparent thickness larger than the remainder and inevitably becomes bulky. The partial bulkiness requires much labor and time for operation of packaging the undergarment one by one or a plurality of undergarments together because the partially bulky portions of the undergarment must be compressed during the operation of packaging the undergarment.

SUMMARY OF THE INVENTION

It is an object of the present invention to provide a disposable pull-on undergarment adapted to be folded so that the individual undergarment or a set of undergarments may be easily packaged.

According to the present invention, there is provided a disposable pull-on undergarment having a front waist region, a rear waist region and a crotch region therebetween, the undergarment comprising a liquid-pervious topsheet, a liquid-impervious backsheet and a liquid-absorbent core disposed between the topsheet and the backsheet, the front and rear waist regions being joined to each other along transversely opposite side edges thereof to form a waist-opening and a pair of leg-openings, the waist-opening being provided with an elastic member extending under tension along its peripheral edge and the leg-openings being provided with elastic means under tension wherein the elastic means associated with the respective leg-openings extend along respective peripheral edges thereof so that each of the elastic means is spaced from the adjacent one of transversely opposite side edges of the absorbent core by a distance which is larger in any one of the front and rear waist regions than in the other of the front and rear waist regions as measured substantially in a middle zone of the crotch region.

In the disposable pull-on undergarment, the present invention is characterized by that, along a folding line extending in a transverse direction to divide the undergarment in upper and lower halves, the undergarment is folded toward any one of the front and rear waist regions in which the foresaid distance is relatively large so that the upper and lower halves are placed one upon another.

According to one embodiment of the present invention, the elastic means associated with each of the leg-openings comprise a first elastic member and a second elastic member having intermediate portions thereof extending across the absorbent core in the crotch region and the remaining portions extending laterally from opposite ends of respective the intermediate portions so that the remaining portions of the first elastic member extend substantially over front halves of the leg-openings in the front waist region while the remaining portions of the second elastic member extend substantially over rear halves of the leg-openings in the rear waist region.

DETAILED DESCRIPTION OF THE PREFERRED EMBODIMENT

Details of a disposable pull-on undergarment according to the present invention will be more fully understood from the description given hereunder with reference to the accompanying drawings.

Figure 1:
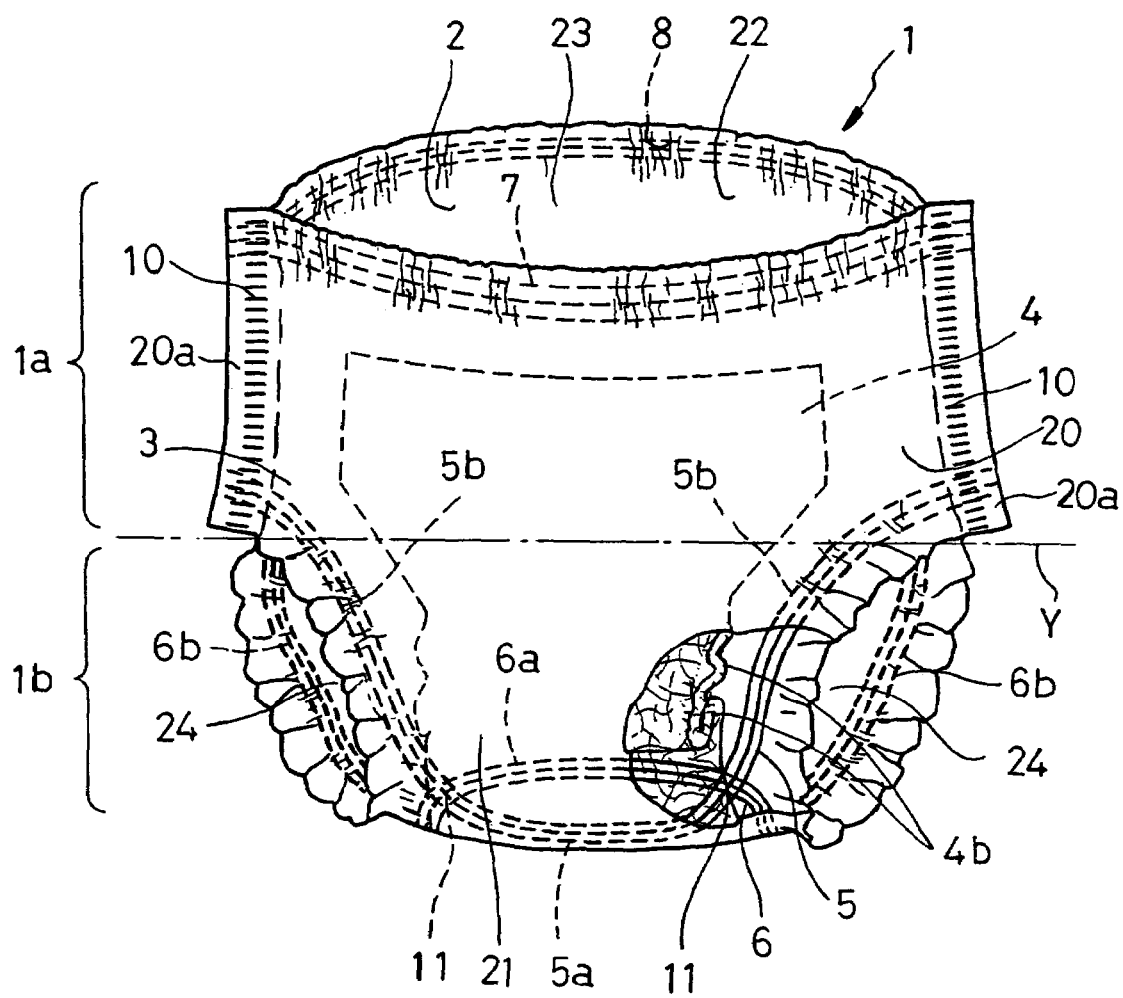
FIG. 1 is a perspective view showing a partly cutaway disposable pull-on undergarment according to the present invention.
Figure 2:
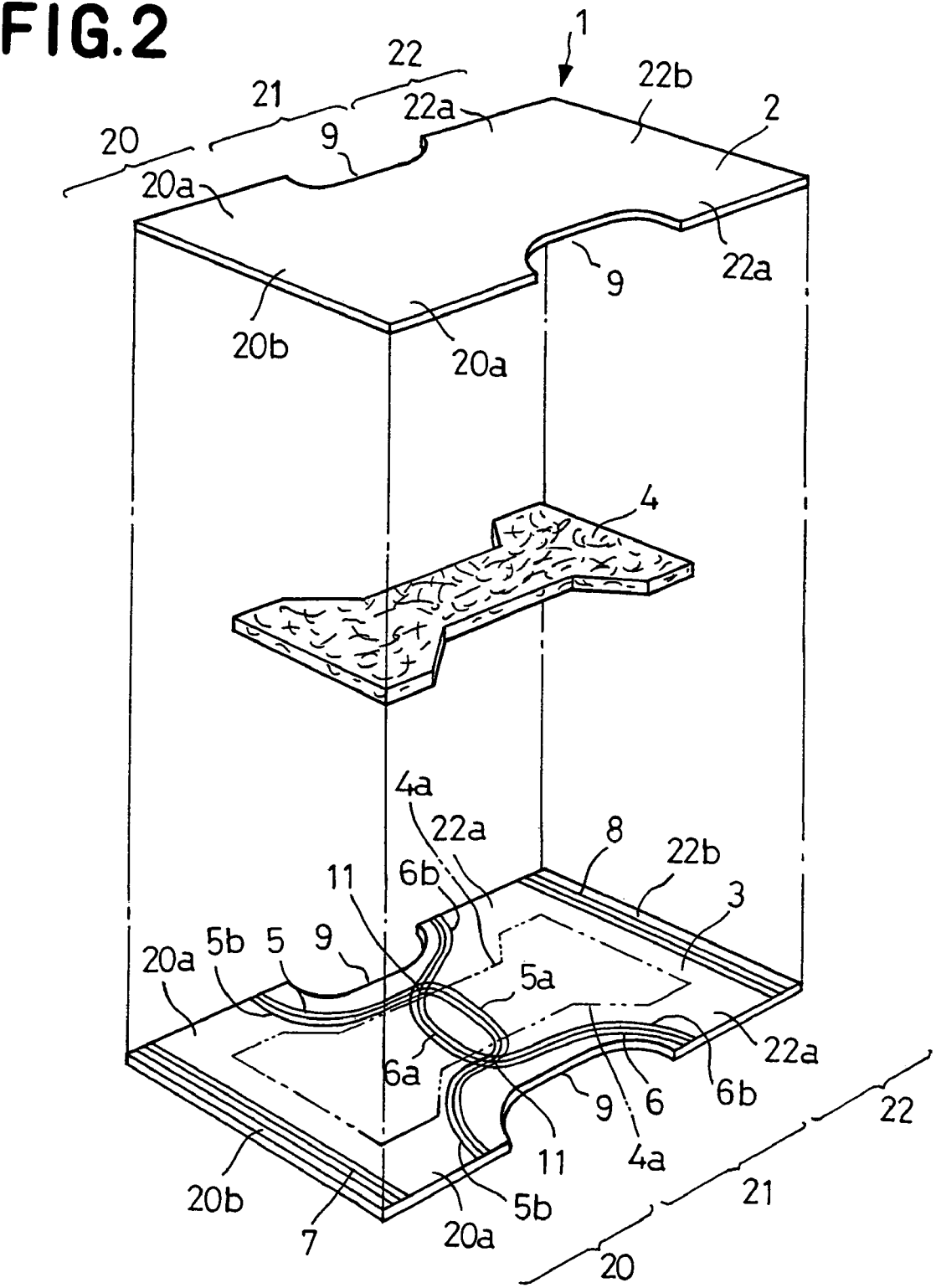
FIG. 2 is an exploded perspective view of the same undergarment.

FIG. 1 is a perspective view showing a partly cutaway disposable pull-on undergarment 1 and FIG. 2 is an exploded perspective view of the same undergarment 1. The undergarment 1 comprises a flexible liquid-pervious topsheet 2, a flexible liquid-impervious backsheet 3 and a semi-rigid hourglass-shaped liquid-absorbent core 4 disposed between the two sheets 2, 3 and joined to the inner surface of at least one of the two sheets 2, 3. Configurationally, the undergarment 1 is composed, in its longitudinal direction orthogonal to its transverse direction, of a front waist region 20, a rear waist region 22 and a crotch region 21 extending between these two waist regions 20, 22.

The front and rear waist regions 20, 22 of the undergarment 1 are joined to each other in the vicinity of their respective side edges 20a, 22a with the outermost narrow portions thereof being left free and thereby a waist-opening 23 and a pair of leg-openings 24 are formed. The side edges 20a, 22a are joined together by a plurality of joining lines 10 intermittently arranged substantially at regular intervals in the longitudinal direction of the undergarment 1 and extending in parallel one to another in the transverse direction of the undergarment 1.

The waist-opening 23 is provided with elastic members 7, 8 transversely extending along respective ends 20b, 22b of the front and rear waist regions 20, 22, respectively. These elastic members 7, 8 are disposed between the topsheet 2 and the backsheet 3 and secured under tension to the inner surface of at least one of these sheets 2, 3.

Transversely opposite side edges of the crotch region 21 are formed with cutouts 9, 9 which are curved inwardly of the undergarment 1 and destined to define the respective leg-openings 24. Along these cutouts 9, respective elastic means each comprising a first elastic member 5 and a second elastic member 6 are disposed between the topsheet 2 and the backsheet 3 and secured under tension to the inner surface of at least one of these two sheets 2, 3. Bonding of these elastic members may be performed utilizing hot melt adhesive agent or a suitable sealing technique such as heat-sealing or ultrasonic sealing.

Intermediate portions 5a, 6a of the first and second elastic members 5, 6 extend in the crotch region 21 following courses deflected toward the rear and front waist regions 22, 20, respectively. The first and second elastic members 5, 6 extend across the absorbent core 4 before they intersect each other at respective opposite ends 11 of the intermediate portions 5a, 6a. Portions 5b, 6b of the first and second elastic members 5, 6 extending laterally beyond the intersecting ends 11 further extend along the respective cutouts 9. The portions 5b of the first elastic member 5 extend substantially over front halves of the respective leg-openings 24 in the front waist region 20 while the portions 6b of the second elastic member 6 extend substantially over rear halves of the respective leg-openings 24 in the rear waist region 22.

The intermediate portions 5a, 6a of the first and second elastic members 5, 6 extend just below the middle zone of the absorbent core 4 without being bonded to the backsheet 3. It should be understood here that the intermediate portions 5a, 6a of the first and second elastic members 5, 6 may be bonded to the backsheet 3, if it is desired. It is also possible without departing from the scope of the present invention to space the intermediate portions 5a, 6a of the first and second elastic members 5, 6 from each other in the longitudinal direction of the undergarment 1 instead of guiding them to intersect each other, or to place the intermediate portions 5a, 6a in contact with each other.

A distance by which the side edge portions 6b of the second elastic member 6 are spaced from the corresponding side edges 4a of the absorbent core 4 as indicated by an imaginary line is larger than a distance by which the laterally extending portions 5b of the first elastic member 5 are spaced from the corresponding side edges 4a of the absorbent core 4. If the portions 5b of the first elastic member 5 are placed closely adjacent to the side edges 4a of the absorbent core 4 so that a contractile force of the first elastic member 5 may be correspondingly increased, the portion of the absorbent core 4 lying in the front waist region 20 will be more tightly put against the wearer's skin. However, such placement of the portions 5b may result in formation of undesirable creases 4b on the core 4.

In the undergarment 1, it is also possible without departing from the scope of the present invention to arrange the undergarment 1 in such a manner in which the first elastic member 5 presents a stretch stress higher than a stretch stress presented by the second elastic member 6. Such arrangement can be achieved by securing the first elastic member 5 to the topsheet 2 and/or the backsheet 3 with a tension higher than a tension with which the second elastic member 6 is secured to the topsheet 2 and/or the backsheet 3, so far as these first and second elastic members 5, 6 are identical to each other in the material, the number of elements constituting each elastic member and the total cross-sectional area. Alternatively, the material, the number of constituting elements and the total cross-sectional area for the first elastic member 5 may differ from those for the second elastic member 6. While the portions 5b of the first elastic member 5 can be put against the wearer's skin more tightly than the portions 6b of the second elastic member 6 by adjusting the stretch stress of the first elastic member 5 higher than the stretch stress presented by the second elastic member 6, such adjustment may result in formation of undesirable creases on the portion of the absorbent core 4 lying in the front waist region 20.

Figure 3:
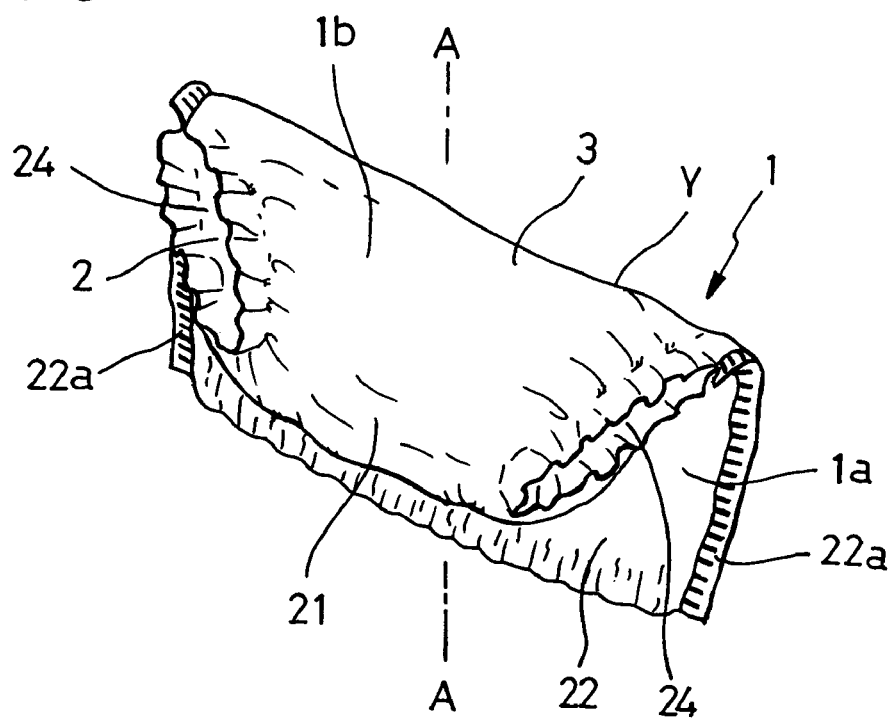
FIG. 3 is a perspective view showing the same undergarment as folded in two.

FIG. 3 is a perspective view showing the undergarment 1 as folded in two. Along a folding line Y (See FIG. 1) transversely extending to divide the undergarment 1 in an upper half 1a and a lower half 1b in the vertical direction, the undergarment 1 is folded toward the rear waist region 22 so that said upper and lower halves 1a, 1b may be placed one upon another.

Figure 4:
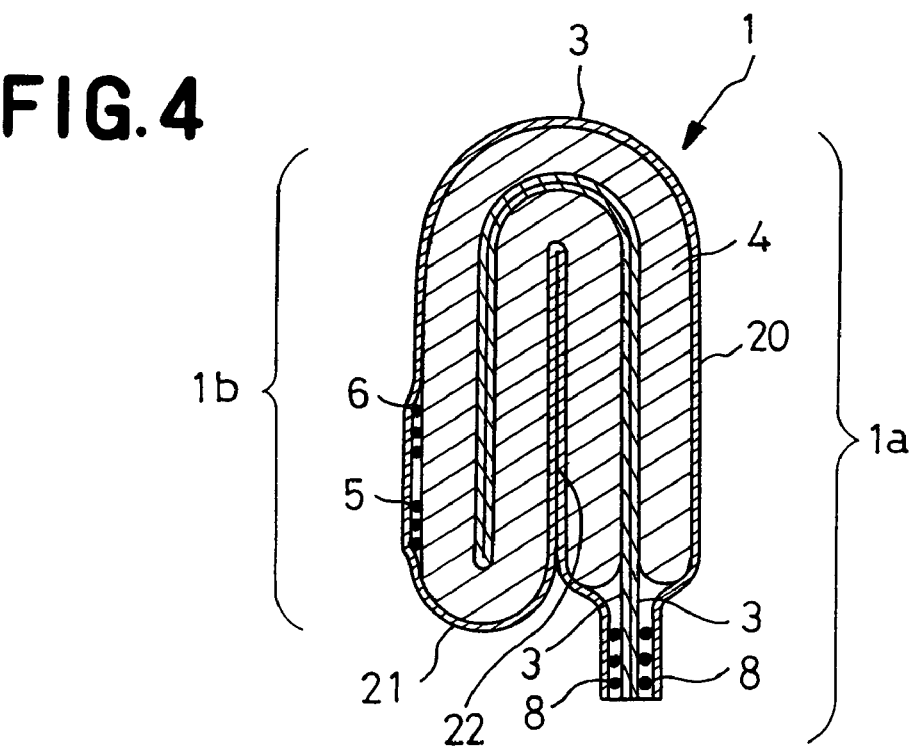
FIG. 4 is a sectional view taken along a line A—A in FIG. 3.

FIG. 4 is a sectional view taken along a line A—A in FIG. 3. Of the absorbent core 4 folded one upon another along the folding line Y, an upper layer is stretched in the longitudinal direction by a thickness of a lower layer. Consequently, the creases 4b on the section of the absorbent core 4 lying in the front waist region 20 which have been formed under the contractile force of the first elastic member 5 before the absorbent core 4 has been folded are smoothed down and a partial bulkiness of the absorbent core 4 is eliminated.

It is also possible to arrange the undergarment 1 so that a distance by which each of the portions 5b of the first elastic member 5 is spaced from each of the side edges 4a of the absorbent core 4 is larger than a distance by which each of the portions 6b of the second elastic member 6 is spaced from each of the side edges 4a of the absorbent core 4. In this case, a section of the absorbent core 4 lying in the rear waist region 22 is apt to be formed with the creases 4b. To avoid this, the undergarment 1 may be folded along the folding line Y toward the front waist region 20 so that the upper half 1*a* may be placed upon the lower half 1*b*.

For the topsheet 2, a hydrophobic nonwoven fabric treated with hydrophiling agent or a hydrophilic nonwoven fabric formed by fibers mixed with hydrophiling agent may be used as stock material. Such nonwoven fabric may be replaced by an apertured thermoplastic synthetic resin film.

For the backsheet 3, stock material having a high flexibility, for example, a synthetic resin film or a laminate sheet comprising such synthetic resin film and hydrophobic nonwoven fabric may be used. The absorbent core 4 comprises a mixture of fluff pulp and superabsorptive polymer particles or the mixture added with core shaping fibers. Such mixture is compressed to a desired thickness and then entirely covered with liquid-pervious sheet such as tissue paper so as to have a semi-rigidity.

The present invention is applicable to an undergarment in which, in addition to the elastic members 7, 8 extending along the peripheral edges of the waist-opening 23, a plurality of elastic members transversely extending across both the front waist region 20 and the rear waist region 22 are disposed between the topsheet 2 and the backsheet 3 and secured under tension to the inner surface of at least one of these sheets 2, 3. Assumed that the plurality of additional elastic members are provided, the portions of the absorbent core 4 underlying the intermediate portions 5*a*, 6*a* of the first and second elastic members 5, 6 and the additional elastic members are apt to be creased. As a result, the absorbent core 4 may partially becomes bulky. However, the undergarment 1 may be folded along the folding line Y to smooth down such creases and thereby to eliminate a partial bulkiness of the undergarment 1.

With the disposable pull-on undergarment provided by the present invention, the undergarment may be folded along the folding line toward the front or rear waist region in which the distance by which each leg-opening's elastic member is spaced from each of the side edges of the absorbent core so that the upper and lower halves of the undergarment may be placed upon each other. In this manner, the creases formed on the portion of the core in the front or rear waist region before the undergarment has been folded in two can be smoothed down and thereby any creases formed on the undergarment, i.e., the partial bulkiness of the undergarment can be eliminated. Accordingly, operation of individually packaging the undergarment of packaging a plurality of undergarments together can be facilitated.

What is claimed is:

1. A disposable pull-on undergarment comprising
  a front waist region;
  a rear waist region;
  a crotch region which extends between the front waist region and the rear waist region;
  a liquid-pervious topsheet;
  a liquid-impervious backsheet; and
  a liquid-absorbent core disposed between said liquid-pervious topsheet and said liquid-impervious back sheet,
  said front and rear waist regions being joined to each other along transversely opposite side edges thereof to form a waist-opening and a pair of leg-openings,
  said disposable pull-on undergarment further comprising an elastic member extending under tension along a peripheral edge of the waist-opening and elastic means provided under tension adjacent the pair of leg-openings, said elastic means being directly secured to at least said backsheet,
  said elastic means associated with respective ones of the pair of leg-openings extending along respective peripheral edges thereof so that portions of the elastic means may be spaced from each of transversely opposite side edges of said liquid-absorbent core by a distance which is larger in said rear waist region than in said front waist region as measured substantially in a middle zone of said crotch region,
  said elastic means associated with each of said pair of leg-openings further comprise a first elastic member and a second elastic member each having intermediate portions thereof extending laterally across the crotch region,
  said disposable pull-on undergarment being folded along a folding line which extends in a transverse direction to divide said undergarment substantially in half into an upper half and a lower half so that said front waist region lies outside said rear waist region, and all intermediate portions of first and second elastic members are positioned on an outward side of the folded diaper exclusively on the same side of the folding line, whereby said front waist region is stretched in a longitudinal direction of said undergarment.

2. A disposable pull-on undergarment according to claim 1, wherein said intermediate portions of said first and second elastic member extend between said liquid-impervious backsheet and said liquid-absorbent core in said crotch region and remaining portions of said first and second elastic members extending laterally from opposite ends of said respective intermediate portions so that said remaining portions of said first elastic member extending substantially over front halves of said leg-opening in said front waist region while said remaining portions of said second elastic member extend substantially over rear halves of said leg-openings in said rear waist region.

* * * * *